US012637605B2

(12) United States Patent
Somerville et al.

(10) Patent No.: US 12,637,605 B2
(45) Date of Patent: May 26, 2026

(54) LIGNIN-BASED COMPOSITIONS AND RELATED METHODS

(71) Applicant: LignoSol IP Limited, San Gwann (MT)

(72) Inventors: Desmond Alexander Somerville, San Gwann (MT); Patrick Dieter Waibel, San Gwann (MT)

(73) Assignee: LignoSol IP Limited, San Gwann (MT)

( * ) Notice: Subject to any disclaimer, the term of this patent is extended or adjusted under 35 U.S.C. 154(b) by 88 days.

(21) Appl. No.: 18/285,525

(22) PCT Filed: Apr. 5, 2022

(86) PCT No.: PCT/IB2022/053161
§ 371 (c)(1),
(2) Date: Oct. 4, 2023

(87) PCT Pub. No.: WO2022/214961
PCT Pub. Date: Oct. 13, 2022

(65) Prior Publication Data
US 2024/0182772 A1      Jun. 6, 2024

(30) Foreign Application Priority Data

Apr. 6, 2021   (GB) ...................................... 2104877
Nov. 8, 2021   (GB) ...................................... 2115987

(51) Int. Cl.
*C09K 8/20*          (2006.01)
*C09K 8/582*         (2006.01)
(Continued)

(52) U.S. Cl.
CPC .............. *C09K 8/203* (2013.01); *C09K 8/582* (2013.01); *C09K 8/584* (2013.01); *C12N 1/20* (2013.01);
(Continued)

(58) Field of Classification Search
CPC ........ C09K 8/203; C09K 8/582; C09K 8/584; C09K 8/594; C09K 2208/10;
(Continued)

(56) References Cited

U.S. PATENT DOCUMENTS 3,438,895 A      4/1969  Edmonsond et al.
3,864,276 A  *   2/1975  Benko .................. C09K 23/017
                                                    516/77
(Continued)

FOREIGN PATENT DOCUMENTS

CA       1132452 A       9/1982
CA       2425424 A1      4/2002
(Continued)

OTHER PUBLICATIONS

Beisl et al., "Lignin from Micro- to Nanosize: Production Methods." Int. Journal of Molecular Sciences. 18(6): 1244 (Jun. 10, 2017) (31 pages).
(Continued)

*Primary Examiner* — Aiqun Li
(74) *Attorney, Agent, or Firm* — Clark & Elbing LLP

(57)          ABSTRACT

Compositions are provided for hydrocarbon applications. In some embodiments, the composition comprises lignin, in particular technical lignin, comprising at least one of lignin nanoparticles and lignin microparticles, preferably wherein at least 20% of the lignin particles are nanoparticles, and at least one strain of bacteria capable of biosurfactant production and/or a biosurfactant produced by at least one such isolated strain of bacteria. Also provided is a related method for making the composition.

11 Claims, 2 Drawing Sheets

(51) Int. Cl.
 *C09K 8/584*  (2006.01)
 *C12N 1/20*  (2026.01)
 *C12R 1/10*  (2006.01)
 *C12R 1/125*  (2006.01)

(52) U.S. Cl.
 CPC ...... *C09K 2208/10* (2013.01); *C09K 2208/24*
  (2013.01); *C12R 2001/10* (2021.05); *C12R*
  *2001/125* (2021.05)

(58) Field of Classification Search
 CPC ............ C09K 2208/24; C12R 2001/10; C12R
  2001/125; C12R 2001/07
 See application file for complete search history.

(56)      References Cited

U.S. PATENT DOCUMENTS

| | | | |
|---|---|---|---|
| 4,101,394 A | 7/1978 | Johnson | |
| 4,133,385 A | 1/1979 | Kalfoglou | |
| 4,304,572 A | 12/1981 | Wiese et al. | |
| 4,392,941 A | 7/1983 | Roth et al. | |
| 4,877,517 A | 10/1989 | Bulatovic et al. | |
| 5,028,238 A | 7/1991 | von Rybinski et al. | |
| 5,059,332 A | 10/1991 | Satoh | |
| 5,114,597 A | 5/1992 | Rayborn et al. | |
| 5,164,480 A | 11/1992 | Huibers et al. | |
| 5,246,602 A | 9/1993 | Forrest | |
| 5,248,329 A | 9/1993 | Rusin et al. | |
| 5,316,664 A | 5/1994 | Gregoli et al. | |
| 5,316,682 A | 5/1994 | Keyser et al. | |
| 5,344,625 A | 9/1994 | Clough | |
| 5,368,972 A | 11/1994 | Yamashita et al. | |
| 5,711,383 A | 1/1998 | Terry et al. | |
| 5,743,945 A * | 4/1998 | Yamashita | C09D 11/38 |
| | | | 106/31.86 |
| 5,911,276 A | 6/1999 | Kieke | |
| 6,306,800 B1 | 10/2001 | Samuel et al. | |
| 6,348,436 B1 | 2/2002 | Langlois et al. | |
| 8,450,260 B2 | 5/2013 | Crawford et al. | |
| 8,455,226 B2 | 6/2013 | De Windt et al. | |
| 8,741,256 B1 * | 6/2014 | Harrison | C01D 7/07 |
| | | | 423/427 |
| 8,748,153 B2 | 6/2014 | Tadic et al. | |
| 10,362,786 B2 | 7/2019 | Chen et al. | |
| 10,829,833 B2 | 11/2020 | Gos et al. | |
| 12,275,894 B2 | 4/2025 | Somerville et al. | |
| 2002/0044887 A1 | 4/2002 | Jones | |
| 2006/0177661 A1 | 8/2006 | Smith et al. | |
| 2007/0045198 A1 | 3/2007 | Sugiura | |
| 2009/0011972 A1* | 1/2009 | Suzuki | C11D 1/722 |
| | | | 510/421 |
| 2009/0082227 A1 | 3/2009 | Hnatow et al. | |
| 2009/0211960 A1 | 8/2009 | Nilsen et al. | |
| 2009/0266541 A1 | 10/2009 | Reynolds et al. | |
| 2009/0291861 A1 | 11/2009 | Sawdon | |
| 2009/0308612 A1* | 12/2009 | Weaver | C09K 8/42 |
| | | | 166/305.1 |
| 2010/0137168 A1 | 6/2010 | Quintero et al. | |
| 2010/0233050 A1 | 9/2010 | Gargulak et al. | |
| 2012/0247763 A1 | 10/2012 | Rakitsky et al. | |
| 2013/0274150 A1 | 10/2013 | Holt et al. | |
| 2014/0261077 A1 | 9/2014 | Merck et al. | |
| 2014/0371071 A1 | 12/2014 | Nitsche | |
| 2015/0166836 A1 | 6/2015 | Liu et al. | |
| 2015/0285051 A1 | 10/2015 | Miller et al. | |
| 2016/0168272 A1 | 6/2016 | Retsina et al. | |
| 2016/0236158 A1 | 8/2016 | Bauer | |
| 2017/0029691 A1 | 2/2017 | Faust, Jr. et al. | |
| 2017/0306264 A1* | 10/2017 | Peggau | C11D 1/825 |
| 2018/0148632 A1 | 5/2018 | Bennett et al. | |
| 2018/0265794 A1 | 9/2018 | Dahlstrand et al. | |
| 2018/0355446 A1 | 12/2018 | Medoff et al. | |
| 2019/0031945 A1 | 1/2019 | Guo et al. | |
| 2019/0055459 A1 | 2/2019 | Zelenev et al. | |
| 2019/0093463 A1 | 3/2019 | Hardin et al. | |

| | | | |
|---|---|---|---|
| 2019/0184350 A1 | 6/2019 | Terasaka et al. | |
| 2019/0382649 A1 | 12/2019 | Jiang et al. | |
| 2019/0390405 A1 | 12/2019 | Geigle et al. | |
| 2020/0032128 A1 | 1/2020 | Farmer et al. | |
| 2020/0157408 A1* | 5/2020 | Farmer | C09K 8/582 |
| 2020/0172788 A1 | 6/2020 | Farmer et al. | |
| 2020/0255466 A1 | 8/2020 | Lintinen et al. | |
| 2020/0352016 A1 | 11/2020 | Bohdy | |
| 2021/0261451 A1 | 8/2021 | Patton | |
| 2021/0261459 A1 | 8/2021 | Alibek et al. | |

FOREIGN PATENT DOCUMENTS

| | | | |
|---|---|---|---|
| CA | 2535702 A1 | 3/2005 | |
| CA | 2547100 A1 | 11/2006 | |
| CA | 2640005 A1 | 8/2007 | |
| CA | 2661202 C | 11/2011 | |
| CA | 2723591 C | 7/2013 | |
| CA | 2705147 C | 9/2014 | |
| CA | 2921996 A1 | 3/2015 | |
| CA | 2693008 C | 4/2016 | |
| CA | 2988826 A1 | 12/2016 | |
| CA | 2791256 C | 6/2017 | |
| CA | 3048404 A1 | 7/2018 | |
| CA | 3052048 A1 | 8/2018 | |
| CA | 3052465 A1 | 8/2018 | |
| CA | 3054686 A1 | 9/2018 | |
| CA | 3058761 A1 | 10/2018 | |
| CA | 2999599 C | 12/2019 | |
| CA | 2772395 C | 1/2020 | |
| CA | 2720739 C | 4/2020 | |
| CA | 2950089 C | 4/2020 | |
| CA | 2831902 C | 5/2020 | |
| CA | 2877367 C | 12/2020 | |
| CA | 2945194 C | 7/2022 | |
| CA | 2886934 C | 1/2023 | |
| CN | 85105225 A | 7/1986 | |
| CN | 101104177 A | 1/2008 | |
| CN | 104152129 A | 11/2014 | |
| CN | 104321422 A | 1/2015 | |
| CN | 103636599 B | 3/2015 | |
| CN | 205527917 U | 8/2016 | |
| CN | 106188857 A | 12/2016 | |
| CN | 108441223 A | 8/2018 | |
| CN | 106217826 B | 9/2018 | |
| CN | 108623112 A | 10/2018 | |
| CN | 109943299 A | 6/2019 | |
| CN | 110616062 A | 12/2019 | |
| GB | 2514202 A | 11/2014 | |
| GB | 2605591 A | 10/2022 | |
| JP | 2011-121002 A | 6/2011 | |
| JP | 2017029892 A | 2/2017 | |
| KR | 101711607 B1 | 3/2017 | |
| KR | 10-2018-0130070 A | 12/2018 | |
| RU | 2188935 C1 | 9/2002 | |
| WO | WO-1992/19349 A1 | 11/1992 | |
| WO | WO-2005/028592 A1 | 3/2005 | |
| WO | WO-2012/151524 A2 | 11/2012 | |
| WO | WO-2013/037643 A1 | 3/2013 | |
| WO | WO-2015/065981 A1 | 5/2015 | |
| WO | WO-2016/053345 A1 | 4/2016 | |
| WO | WO-2016/196680 A1 | 12/2016 | |
| WO | WO-2018/064689 A1 | 4/2018 | |
| WO | WO-2019/067356 A1 | 4/2019 | |
| WO | WO-2019/112970 A1 | 6/2019 | |
| WO | WO-2019/191296 A1 | 10/2019 | |
| WO | WO-2019/213055 A1 | 11/2019 | |
| WO | WO-2020/028253 A1 | 2/2020 | |
| WO | WO-2020/060529 A1 | 3/2020 | |
| WO | WO-2020/072735 A1 | 4/2020 | |
| WO | WO-2020/149756 A2 | 7/2020 | |
| WO | WO-2020/264073 A1 | 12/2020 | |
| WO | WO-2021/015633 A1 | 1/2021 | |
| WO | WO-2021/052939 A1 | 3/2021 | |

OTHER PUBLICATIONS

Bicca et al., "Production of Biosurfactant by Hydrocarbon Degrading Rhodococcus Ruber and Rhodococcus Erythropolis." Revista de Microbiologia. 30: 231-236 (1999) (6 pages).

(56) References Cited

OTHER PUBLICATIONS

Chang et al., "A novel nano-lignin-based amphoteric copolymer as fluid-loss reducer in water-based drilling fluids." Colloids and Surfaces A. 583:123979 (Sep. 21, 2019) (10 pages).

Hruzová et al., "Organosolv lignin hydrophobic micro- and nanoparticles as a low-carbon footprint biodegradable flotation collector in mineral flotation." Bioresource Technology. 306:123235 (Mar. 23, 2020) (4 pages).

International Search Report and Written Opinion for International Application No. PCT/IB22/53145 mailed Jun. 27, 2022 (9 pages).

International Search Report and Written Opinion for International Application No. PCT/IB22/53147 mailed Jun. 15, 2022 (9 pages).

International Search Report and Written Opinion for International Application No. PCT/IB22/53148 mailed Jun. 27, 2022 (9 pages).

International Search Report and Written Opinion for International Application No. PCT/IB22/53151 mailed Jun. 29, 2022 (9 pages).

International Search Report and Written Opinion for International Application No. PCT/IB22/53158 mailed Jun. 21, 2022 (8 pages).

International Search Report and Written Opinion for International Application No. PCT/IB22/53160 mailed Jun. 29, 2022 (7 pages).

International Search Report and Written Opinion for International Application No. PCT/IB22/53161 mailed Jun. 27, 2022 (6 pages).

International Search Report and Written Opinion for International Application No. PCT/IB22/53162 mailed Jul. 1, 2022 (7 pages).

Li, Qingxin, "Rhamnolipid synthesis and production with diverse resources." Front. Chem. Sci. Eng. 11(1): 27-36 (Mar. 22, 2017) (10 pages).

Negi et al., "A review on lignin utilization in petroleum exploration, petroleum products formulation, bio-fuel production, and oil spill clean-up." Biomass Conversion and Biorefinery. 13: 1417-1428 (Nov. 5, 2020) (12 pages).

Sauki et al., "Extracted Lignin from Rhizophora's Black Liquor as Fluid Loss Control Additive in Water Based Drilling Mud." Key Engineering Materials. 755: 74-80 (Aug. 20, 2018) (8 pages).

Schneider et al., "Assessment of Morphological, Physical, Thermal, and Thermal Conductivity Properties of Polypropylene/ Lignosulfonate Blends." Materials. 14(3): 543 (Jan. 23, 2021) (10 pages).

Search and Examination Report for Application No. GB2104859.0, dated May 11, 2021 (8 pages).

Search and Examination Report for Application No. GB2104860.8, dated May 4, 2021 (8 pages).

Search and Examination Report for Application No. GB2104862.4, dated May 21, 2021 (8 pages).

Search and Examination Report for Application No. GB2104865.7, dated Jun. 8, 2021 (8 pages).

Search and Examination Report for Application No. GB2104869.9, dated Apr. 16, 2021 (6 pages).

Search and Examination Report for Application No. GB2104870.7, dated Jun. 2, 2021 (7 pages).

Search and Examination Report for Application No. GB2104877.2, dated May 10, 2021 (6 pages).

Search and Examination Report for Application No. GB2104883.0, dated May 4, 2021 (8 pages).

Search and Examination Report for Application No. GB2115987.6, dated Dec. 15, 2021 (6 pages).

Solihat et al., "Lignin as an Active Biomaterial: A Review." Jurnal Sylva Lestari. 9(1): 1-22 (Jan. 2021) (22 pages).

EP Application No. EP4320192, Extended European Search Report (EESR), Search Opinion, and Supplementary Search Report, dated Jan. 17, 2025 (11 pages).

GB Application No. GB2116007.2, Search and Examination Report, dated Nov. 25, 2021 (8 pages).

GB Application No. GB2214123.8, Search and Examination Report, dated Nov. 18, 2022 (8 pages).

Madhu, "Difference Between Anolyte and Catholyte", published Online Sep. 19, 2020 at: https://www.differencebetween.com/difference-between-anolyte-and-catholyte/ (3 pages).

Nazari et al., "Study relationships between flotation variables and recovery of coarse particles in the absence and presence of nanobubble," Colloids and Surfaces A: Physicochemical and Engineering Aspects 559:284-8 (Sep. 27, 2018).

PCT Application No. PCT/IB22/59176, International Search Report (ISR) and Written Opinion, mailed Jan. 26, 2023 (9 pages).

PCT Application No. PCT/IB23/59500, International Search Report (ISR) and Written Opinion, mailed Feb. 2, 2024 (8 pages).

Schneider et al., "Assessment of Morphological, Physical, Thermal, and Thermal Conductivity Properties of Polypropylene/ Lignosulfonate Blends", Materials, (Jan. 2021) vol. 14; 543 (10 pages).

This vs. That: Anolyte vs. Catholyte, published Online at: https://thisvsthat.io/anolyte-vs-catholyte (2023) (2 pages).

Arapova et al., "Lignin: A Renewable Resource of Hydrocarbon Products and Energy Carriers (Review)", Petrochemistry. (2020) vol. 60, No. 3, pp. 251-269 (English Translation) (38 pages).

Filonov et al., "Bioremediation of Oil-Contaminated Soils in the Republic of Belarus Using the Biopreparation 'Microbak' and a Sorbent based on Lignin", Puschchino Conference Proceedings: Biochemistry, Physiology and Biosphere: the Role of Microorganisms, Dec. 2-6, 2019 (English Translation) (8 pages).

Lazareva et al., "Pseudomonas aeruginosa: Pathogenicity, Pathogenesis and Diseases", (English Abstract Only) (2015) vol. 17, No. 3, pp. 170-184 (17 pages).

Saikia et al., "Isolation of biosurfactant-producing Pseudomonas aeruginosa RS29 from oil-contaminated soil and evaluation of different nitrogen sources in biosurfactant production", Ann. Microbiol. (Jul. 2011) vol. 62, pp. 753-763 (11 pages).

\* cited by examiner

100

| | |
|---|---|
| Provide lignin | 102 |

↓

| | |
|---|---|
| Provide at least one isolated strain of bacteria capable of biosurfactant production | 104 |

↓

| | |
|---|---|
| Combine the lignin and the at least one isolated strain | 106 |

LIGNIN-BASED COMPOSITIONS AND RELATED METHODS

CROSS-REFERENCE TO RELATED APPLICATIONS

This application claims priority to GB Provisional Patent Application No. 2104877.2, filed 6 Apr. 2021, and GB Provisional Patent Application No. 2115987.6, filed 8 Nov. 2021, the disclosures of which are hereby incorporated by reference in their entireties.

BACKGROUND OF THE INVENTION

The present disclosure relates to lignin-based compositions for hydrocarbon applications and related methods.

Hydrocarbons, including natural gas and oil (petroleum), may be extracted from subterranean reservoirs by a variety of means. In conventional reservoirs, the hydrocarbon is present in discrete accumulations or pools from which the hydrocarbons can readily be extracted via vertical wells drilled into the reservoir. In contrast, unconventional reservoirs typically have low permeability and/or porosity and thus require specialized techniques to extract the hydrocarbons therein.

Some unconventional reservoirs require hydraulic fracturing or "fracking" to allow the hydrocarbons therein to be extracted. Fracking typically involves high-pressure injection of the fracking fluid such as "slick water" into a wellbore to create cracks in rock formations through which hydrocarbons may flow more freely. However, conventional fracking methods may require large volumes of water and may also include environmentally harmful chemicals in the fracking fluid. Processing the produced water from such operations may require costly water treatment methods.

Oil sands, also referred to as tar sands, are another type of unconventional petroleum deposit found in countries such as Canada, Venezuela, Kazahkstan, and Russia. These deposits are typically a complex mixture of particulate matter such as sand, quartz crystal or clay, with heavy oil, extra heavy oil and/or bitumen, and water.

Various techniques exist for extracting oil from oil sands, such as cold heavy oil production with sand (CHOPS), cyclic steam stimulation (CSS), steam assisted gravity drainage (SAGD), vapour extraction (VAPEX), toe to heel air injection (THAI), combustion overhead gravity drainage (COGD), or a combination of these techniques. Some oil sands deposits that are located close to the surface may also be extracted using surface mining techniques, typically followed by a hot or warm water separation process. Each of these techniques have at least one disadvantage of: using large quantities of water; using large amounts of energy; and requiring the use of chemicals that are environmentally harmful and/or costly.

Moreover, hydrocarbon contamination of ground material and/or water due to oil and gas extraction processes, or pipeline leaks, is a significant environmental problem. For example, hot water extraction of surface-mined oil sands produces large volumes of oil sands tailings which typically comprise a mixture of water, sand, quartz crystal, clay, and residual bitumen. Pipeline leaks may produce mixtures of oil and soil or sand, often also with water. Similarly, oil spills at sea may produce mixtures of oil and water. Separation of the hydrocarbons the ground material and/or water may be difficult and expensive.

The use of analogue ionic liquids for the separation of hydrocarbons from particulate matter has been proposed in U.S. Pat. No. 9,447,329. However, the reagents used are costly and may make the process economically infeasible.

SUMMARY OF THE INVENTION

In one aspect of the invention, there is provided a composition comprising lignin and at least one isolated strain of bacteria capable of producing at least one biosurfactant, and/or at least one biosurfactant produced from at least one bacteria capable of producing a biosurfactant, the lignin comprising at least one of lignin nanoparticles and lignin microparticles, in particular at least 20% of the lignin particles being nanoparticles.

In some embodiments, the lignin is technical lignin.

In some embodiments, the technical lignin comprises at least one of Kraft lignin, lignosulfonates, soda lignin, organosolv lignins, steam-explosion lignin, enzymatic hydrolysis lignin, or unhydrolyzed Kraft black liquor lignin.

In some embodiments, the lignin is in an aqueous suspension.

In some embodiments, the at least one isolated strain comprises at least one isolated strain of Bacillus.

In some embodiments, the at least one isolated strain of Bacillus is selected from the group consisting of Bacillus amyloliquefaciens, Bacillus licheniformis, Bacillus pumilus, Bacillus subtilis, and combinations thereof.

In some embodiments, the at least one isolated strain is in the form of a liquid suspension or freeze-dried spores.

In some embodiments, the hydrocarbon separation composition further comprises a catholyte solution.

In some embodiments, the catholyte solution is a stabilized or upgraded catholyte solution.

In some embodiments, the composition further comprises at least one of a carboxylic acid or a salt or ester thereof.

In some embodiments, the carboxylic acid ester comprises a methyl ester or a butyl ester.

In some embodiments, the carboxylic acid or salt or ester thereof comprises a di-carboxylic acid or a salt or ester thereof.

In some embodiments, the composition further comprises carbon black.

In some embodiments, the composition further comprises pyroligneous acid.

In some embodiments, the composition further comprises pyrolysis oil.

In some embodiments, the composition is gasified.

In some embodiments, the composition is gasified with at least one of nanobubbles and microbubbles.

In another aspect, there is provided a method for making a composition, the method comprising providing lignin, in particular technical lignin, and treating the lignin to produce lignin nanoparticles and/or lignin microparticles, preferably wherein at least 20% of the lignin particles are nanoparticles, and providing at least one isolated strain of bacteria capable of producing at least one biosurfactant, and/or at least one biosurfactant produced from at least one isolated strain of bacteria capable of producing a biosurfactant, and combining the lignin with the at least one isolated strain of bacteria and/or at least one biosurfactant.

In some embodiments, the method further comprises adjusting the solids content of the lignin prior to combining the lignin with the at least one isolated strain.

In some embodiments, the method further comprises combining the lignin and at least one isolated strain with a catholyte solution, in particular a stabilized or enhanced catholyte solution In some embodiments, the method further comprises combining at least one of pyroligneous acid, a carboxylic acid or a salt or ester thereof, carbon black, and pyrolysis oil with the lignin prior to combining the lignin and, where included, the catholyte solution, with the at least one isolated strain.

In some embodiments, the method further comprises gasifying the composition with at least one of nanobubbles and microbubbles.

In some embodiments of the invention, the compositions may be used in the recovery and/or processing of hydrocarbons including, for example, hydrocarbon separation, viscosity reduction, demulsification of oil-in-water emulsions, and separation from particulate matter.

Other aspects and features of the present disclosure will become apparent, to those ordinarily skilled in the art, upon review of the following description of specific embodiments of the disclosure.

BRIEF DESCRIPTION OF THE DRAWINGS

The invention will now be described in more detail, by way of example only, with reference to the accompanying drawings in which.

DESCRIPTION OF PREFERRED EMBODIMENTS

Figure 1:
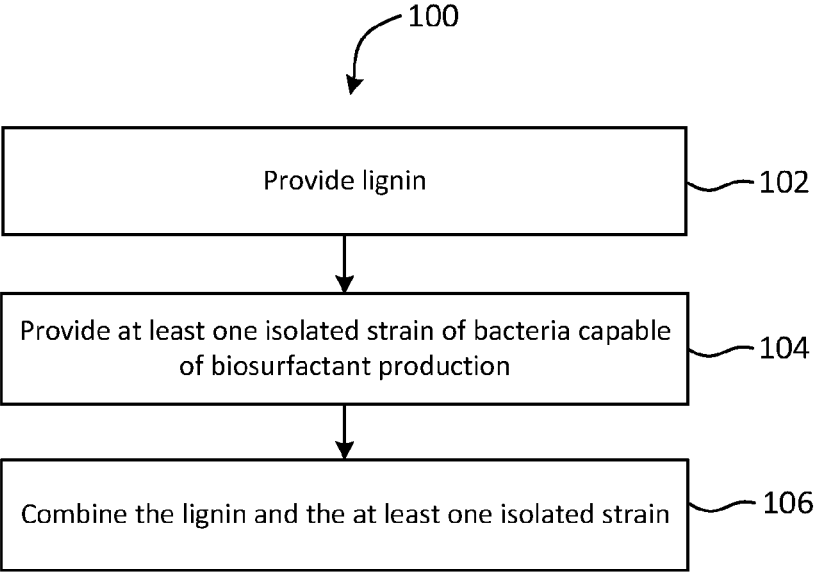
FIG. 1 is a flowchart of an example method for making a composition for separating hydrocarbons from a hydrocarbon-containing material; according to some embodiments.

Generally, the present disclosure provides a composition for hydrocarbon applications. In some embodiments, the composition comprises lignin, in particular technical lignin, comprising at least one of lignin nanoparticles and lignin microparticles, and at least one strain of bacteria capable of biosurfactant production. Also provided is a related method for making a composition of the invention.

As used herein, "lignin" refers to a biopolymer that is found in the secondary cell wall of plants and some algae. Lignin is a complex cross-linked phenolic polymer with high heterogeneity. Typical sources for the lignin include, but are not limited to: softwood; hardwood; and herbaceous plants such as corn stover, bagasse, grass, and straw.

In some embodiments, the lignin comprises technical lignin. As used herein, "technical lignin" refers to lignin that has been isolated from lignocellulosic biomass, for example, as a byproduct of a pulp and paper production or a lignocellulosic biorefinery. Technical lignins may have a modified structure compared to native lignin and may contain impurities depending on the extraction process. In some embodiments, the technical lignin comprises at least one of Kraft lignin, lignosulfonates, soda lignin, organosolv lignin, steam-explosion lignin, and enzymatic hydrolysis lignin. In other embodiments, the technical lignin may comprise any other form of technical lignin.

In embodiments where the lignin comprises lignosulfonates, the lignosulfonates may be in the form of a salt including, for example, sodium lignosulfonate, calcium lignosulfonate, or ammonium lignosulfonate.

In other embodiments, the technical lignin is in the form of unhydrolyzed Kraft black liquor. Black liquor is a byproduct of the Kraft process and may contain not only lignin but hemicellulose, inorganic chemicals used in the pulping process, and other impurities. In other embodiments, the technical lignin is in the form of "brown liquor" (also referred to as red liquor, thick liquor and sulfite liquor) which refers to the spent liquor of the sulfite process. In other embodiments, the technical lignin may be in the form of any other spent cooking liquor of a pulping process or any other suitable lignin-based byproduct.

In other embodiments, the lignin may be synthetic lignin or any other suitable type of lignin.

In some embodiments, the lignin is hydrolyzed. As used herein, "hydrolyze" refers to using acid or base hydrolysis to at least partially separate lignin from the polysaccharide content of the lignocellulosic biomass. For example, where the lignin is in the form of black liquor, carbon dioxide may be used to precipitate Kraft lignin from the black liquor and then the Kraft lignin may be neutralized with sodium hydroxide.

In some embodiments, the lignin is in aqueous suspension. As used herein, an "aqueous suspension" of lignin refers to solid particles of lignin suspended, dispersed, and/or dissolved in a solvent that at least partially comprises water. In some embodiments, the solvent comprises substantially all water. In other embodiments, the solvent may comprise a combination of water and any other suitable solvent.

In some embodiments, the aqueous suspension of lignin may have a solids content of about 10% to about 90%, or about 25% to about 75%, or about 30% to about 60%, or about 33% to about 55% or about 50% to about 60%. In some embodiments, the aqueous suspension of lignin may have a solids content of about 10% or above, or of about 25% or above, or of about 30% or above, or of about 33% or above or of about 50% or above. In some embodiments, the aqueous suspension of lignin may have a solids content of about 90% or below, or of about 75% or below, or of about 60% or below, or of about 55% or below. In some embodiments, the aqueous suspension has a solids content of about 46%. A solids content of about 33% to about 55% may allow the composition to be flowable, which may be preferred for some applications. In other applications, the composition may be used as a slurry and the solids content may be as high as about 85% to about 90%.

As used herein, "nanoparticle" refers to a particle in the nanometer size range, for example, between about 1 nm and about 100 nm, and "microparticle" refers to a particle in the micrometer size range, for example, between about 100 nm and about 1000 μm (1 mm). In some preferred embodiments, the lignin particles have a size of about 200 nm or less, or about 100 nm or less. In some preferred embodiments, at least about 20%, or at least 30%, or at least 40%, or at least 50%, or at least 60%, or at least 70%, or at least 80%, or at least 90% of the lignin particles are nanoparticles having a size of about 100 nm or less.

The lignin nanoparticles and/or microparticles can be produced by any suitable method. For example, the lignin nanoparticles and/or microparticles can be produced using at least one of: solvent shifting; pH shifting; cross-linking polymerization; mechanical treatment; ice-segregation; template based synthesis; aerosol processing; electro spinning; and carbon dioxide ($CO_2$) antisolvent treatment. Such methods are described in Beisl et al. "Lignin from Micro- to Nanosize: Production Methods" *Int. J. Mol. Sci.* 2017; 18: 1244, incorporated herein by reference in its entirety.

In some preferred embodiments, lignin nanoparticles are produced using a pH shifting method, for example, as disclosed in Beisl et al. Briefly, the starting lignin material may be dissolved in a basic solution (e.g. an aqueous NaOH solution at pH 12) and the pH of the solution may be gradually decreased by addition of acid (e.g. $HNO_3$) to precipitate lignin nanoparticles. The solution may then be neutralized (e.g. by addition of NaOH) to resuspend the nanoparticles. The resulting particles may have a size of about 200 nm or less, or about 100 nm or less. In other embodiments, the lignin nanoparticles may be produced by any other suitable method.

By providing the lignin in the form of lignin nanoparticles and/or microparticles, the surface area of the lignin is increased, thereby also increasing the negative force around each particle. In addition, lignin nanoparticles and/or microparticles may have improved solubility in water. Conventional lignins are typically only soluble in water at alkaline pH; however, nanoparticles and/or microparticles may be soluble in approximately neutral water (Beisl et al.), which may be preferred for some applications.

In some embodiments, where the lignin comprises an aqueous suspension of lignin nanoparticles, the zeta potential value of the suspension may be about −5 to about −80 mV. In some embodiments, the specific gravity of the aqueous suspension of lignin nanoparticles is between about 1.286 to about 1.7 SG.

The composition further comprises at least one isolated strain of bacteria capable of biosurfactant production and/or at least one biosurfactant produced from at least one isolated strain of bacteria capable of producing a biosurfactant.

As used herein, "isolated" or "isolate", when used in reference to a strain of bacteria, refers to bacteria that have been separated from their natural environment. In some embodiments, the isolated strain or isolate is a biologically pure culture of a specific strain of bacteria. As used herein, "biologically pure" refers to a culture that is substantially free of other organisms.

As used herein, "biosurfactant" refers to compounds that are produced at the bacterial cell surface and/or secreted from the bacterial cell and function to reduce surface tension and/or interfacial tension. Non-limiting examples of biosurfactants include: lipopeptides, surfactin, glycolipids, rhamnolipids, methyl rhamnolipids, viscosin, and the like. The isolated strain may be capable of producing one or more types of biosurfactants.

In some embodiments, the isolated strain may produce one or more additional active compounds. For example, the isolated strain may produce a biopolymer, solvent, acid, exopolysaccharide, and the like.

In some embodiments, at least one isolated strain of bacteria comprises a strain of *Bacillus*. In other embodiments, at least one isolated strain comprises a strain of bacteria capable of biosurfactant production and that is non-pathogenic. Non-limiting examples of suitable strains are listed in Satpute et al. "Methods for investigating biosurfactants and bioemulsifers: a review" *Critical Reviews in Biotechnology,* 2010, 1-18. For example, the at least one isolated strain of *Bacillus* may be *Bacillus amyloliquefaciens, Bacillus licheniformis, Bacillus pumilus, Bacillus subtilis*, or combinations thereof, in particular *Bacillus licheniformis*.

In some embodiments, the pH of the composition may be selected or adjusted to provide a suitable pH for the isolated strain(s). In some embodiments, the composition may further comprise one or more nutrients to support growth of the bacteria such as, for example, acetate, one or more vitamins, etc.

In some embodiments, the isolated strain is in a viable form. For example, in some embodiments, the isolated strain may be in the form of a liquid suspension. In some embodiments, the isolated strain may be incubated for a suitable period of time prior to incorporation into the composition such that at least a portion of biosurfactant(s) are secreted into the bacterial suspension and therefore can be incorporated into the composition. For example, the bacteria can be incubated/fermented for between about one day and about six months or longer. The isolated strain may be incubated in the presence of a nutrient source and under suitable conditions (e.g. temperature, agitation, etc.) to produce the biosurfactant(s).

In other embodiments, the isolated strain may be in a lyophilized (freeze-dried) form. In some embodiments, the freeze-dried form comprises freeze-dried spores.

In some embodiments, where the isolated strain is in the form of a liquid suspension or in a freeze-dried form, the composition may comprise approximately 40 billion CFU (colony forming units) may be combined with at least about 1 g of lignin and up to several tons of lignin.

In other embodiments, the isolated strain may in an inviable form. For example, the isolated strain may be in the form of heat-killed cells or a cell lysate. In these embodiments, the bacteria of the isolated strain may be incubated for a suitable period of time prior to loss of viability (e.g. heat killing or lysis) such that a sufficient quantity of biosurfactant(s) is secreted into the bacterial suspension for incorporation into the composition. For example, the bacteria may be incubated for at least one week prior to loss of viability.

In other embodiments, a liquid suspension of bacteria may be incubated to produce the biosurfactant(s) and a supernatant containing the biosurfactant(s) may be separated from the bacterial cells and used in the composition.

Without being limited by theory, it is believed that the combination of lignin and the biosurfactant produced by the isolated strain act synergistically to mimic the natural habitat of the biosurfactant producing. The lignin may function as a growth substrate that contains required nutrients (carbon and fructose) to support growth of the bacteria, with the exception of additional acetate and metallic vitamins which may be added to the composition as needed.

In addition, a series of drop collapse tests were conducted to evaluate additional benefits of combining the lignin with a suitable biosurfactant in the composition of the invention. In particular, the tests were carried out to determine the effectiveness of the compositions of the invention in reducing the surface tension of water and other liquids. The results indicated that a further advantage in combining the lignin and biosurfactant in the composition of the invention is a significant reduction in surface tension at concentrations of between about 10 ppm and 300 ppm of the biosurfactant, which assists significantly in the compositions ability to cut through hydrocarbon containing materials.

In some embodiments, the lignin-based compositions of the invention further comprise catholyte solutions. As used herein, "catholyte solution" is an activated solution produced in an electrochemical reaction, and is that part of the electrolyte solution adjacent the cathode of an electrochemical cell. It can be produced, for instance, from a 0.05%-1% salt brine (NaCl or KCl), and has a pH in the range 10.0 to 13.0 and an ORP/Redox value of less than about −800 mV, typically in the order of −900 to −950 mV. In the case of an NaCl starting solution, the active ingredient is highly active, and typically unstable, NaOH.

The compositions of the invention can comprise from about 1% to about 75% by volume of the catholyte solution.

In some embodiments, the composition further comprises at least one of a carboxylic acid or a salt or ester thereof. In some embodiments, the carboxylic acid is a di-carboxylic acid or a salt or ester thereof. The carboxylic acid or salt/ester thereof, may function as a solvent, for example, by facilitating formation of a stable emulsion of the various components of the composition. In some embodiments, the composition comprises a carboxylic acid ester. In some embodiments, the carboxylic acid ester comprises a methyl ester or a butyl ester. In some embodiments, the butyl esters are produced by biochemical metathesis. In some embodiments, the butyl ester comprises n-Butyl 4-oxopentanoate. In some embodiments, the methyl ester comprises unsaturated $C_{10}$ or $C_{12}$ methyl ester. In some embodiments, the methyl ester comprises methyl 9-decenoate or methyl 9-dodecenoate. In some embodiments, the methyl ester is produced from a plant oil feedstock.

In other embodiments the carboxylic acid or a salt or ester thereof may comprise at least one oleic acid or a salt or ester thereof. In some embodiments, the oleic acid or a salt or ester thereof may be provided in the form of "tall oil", a viscous liquid obtained as a byproduct of the Kraft process. In some embodiments, the tall oil may be distilled to tall oil rosin or tall oil fatty acid (TOFA) which comprise a higher proportion of oleic acids than tall oil.

In other embodiments, the carboxylic acid may comprise acetic acid and/or pyroligneous acid, as described in more detail below.

In some embodiments, the composition comprises a combination of two or more carboxylic acids or salts/esters thereof. As one example, the composition may comprise a combination of one or more of: di-carboxylic acid, pyroligneous acid, and butyl esters produced by biochemical metathesis.

In some embodiments, the composition may comprise about 1% to about 30%, or about 1% to about 20%, or about 1% to 10% of di-carboxylic acid and/or pyroligneous acid and/or butyl esters by volume.

In some embodiments, the composition further comprises pyroligneous acid. Pyroligneous acid is also known as wood vinegar or wood acid. The pyroligneous acid may be produced by fast pyrolysis, slow pyrolysis, or any other suitable process. The pyroligneous acid may be produced from any suitable biomass such as, for example, beech biomass. As one example, the pyroligneous acid may be supplied by Nettenergy™ (CAS number 8030-97-5). In some embodiments, the pyroligneous acid comprises about 2% to about 20% acetic acid, or about 5% to about 10% acetic acid, or about 7% acetic acid. In some embodiments, the pyroligneous acid comprises about 2% or above or about 5% or above, and/or about 20% or below or about 10% or below acetic acid. In other embodiments, an aqueous solution of pure or relatively pure acetic acid at the concentrations listed above may be used in place of the pyroligneous acid. The pyroligneous acid may function as a solvent to facilitate dissolution of the composition into the hydrocarbon-containing material in the methods described below. In some embodiments, the pyroligneous acid may also be used as a pre-treatment in methods for recovering hydrocarbon from a subterranean reservoir, as described in more detail below. In some embodiments, the composition may comprise about 1% to about 50%, or about 10% to about 40%, or about 30% pyroligneous acid by volume. In some embodiments, the composition may comprise about 1% or above or about 10% or above pyroligneous acid by volume. In some embodiments, the composition may comprise about 50% or less or about 40% or less pyroligneous acid by volume.

In some embodiments, the composition further comprises carbon black. The carbon black may be electroconductive carbon black and the carbon black may function to increase the conductivity of the composition. In some embodiments, the carbon black may be conductive, superconductive, extra-conductive or ultraconductive carbon black. In some embodiments, the carbon black may be in the form of carbon black beads, microparticles, and/or nanoparticles. For example, the carbon black may comprise Printex™ XE2 B Beads from Orion Engineered Carbons™. In some embodiments, the composition may comprise about 0.5% to about 10% carbon black by volume. In some embodiments, addition of carbon black may increase the negative zeta potential of the composition thereby increasing its electrical stability. In other embodiments, the composition may comprise any other highly conductive microparticle and/or nanoparticle.

Optionally, the composition may further comprise pyrolysis oil. Pyrolysis oil may also be referred to as wood oil. The pyrolysis oil may be produced by fast pyrolysis, slow pyrolysis, or any other suitable process. The pyrolysis oil may be produced from any suitable biomass such as, for example, beech biomass. The pyrolysis oil may act as an odorant to mask the smell of the lignin in the composition. The composition may comprise about 0.1% to about 2%, or about 0.2% to about 1%, or about 0.5% pyrolysis oil by weight. The composition may comprise about 0.1% or above or about 0.2% or above pyrolysis oil by weight. The composition may comprise about 2% or less or about 1% or less pyrolysis oil by weight.

In some embodiments, the composition is gasified with a gas. As used herein, "gasified" refers to introduction of a gas into the composition such that bubbles of the gas are suspended therein. The term "aerated" refers to gasifying with air or oxygen. The gas may be selected based on the aerobic or anaerobic nature of the isolated strain(s) incorporated into the composition. In some embodiments, the gas at least partially comprises oxygen. For example, the gas may be air or relatively pure oxygen. In some embodiments, the gas may at least partially comprise carbon dioxide and/or nitrogen. Gasification may function to provide oxygen and/or other suitable gasses directly or in close proximity to the bacterial cells of the isolated strain. Gasification may promote proliferation of the bacterial cells and allow the composition to be used or stored for an extended period of time. In some embodiments, the aerated composition may have a half-life of about 20 to 30 days.

In some embodiments, the composition is gasified with nanobubbles and/or microbubbles of the gas. As used herein, "nanobubble" refers to bubbles in the nanometer range and "microbubble" refers to bubbles in the micrometer range. The nanobubbles and/or microbubbles may be introduced into the composition by any suitable means including, for example, a micro- or nanobubble nozzle or a venturi tube.

It has surprisingly been found that using a stabilized or upgraded as opposed to an otherwise unstable catholyte solution enhances the action of the compositions of the invention. Accordingly, in some embodiments, the catholyte solution is pre-treated in a system that is designed to introduce nitrogen gas into the catholyte solution, in particular in the form of nano- and/or micro-bubbles, for incorporation into a composition of the invention.

Accordingly, in some embodiments, the catholyte solution is upgraded prior to blending with the other components of the separation composition.

In some embodiments, the composition may comprise any other suitable components. For example, in some embodiments, the composition may further comprise at least one nutrient source for the live bacteria of the isolated strain.

Therefore, in some embodiments, a relatively non-toxic, inert, and sustainable composition is provided for hydrocarbon separation. The composition may also be relatively low cost as lignin is a waste product of pulp and paper operations that is typically discarded.

Also provided herein is a method of making a composition for hydrocarbon separation. The method may be used to make embodiments of the composition described above.

FIG. 1 shows a flowchart of an example method 100 according to some embodiments.

At block 102, lignin is provided. The term "provide" in this context may refer to making, extracting, receiving, buying, or otherwise obtaining the lignin.

The lignin may be any of the lignins described above. In some embodiments, the lignin is provided as an aqueous suspension. In some embodiments, the lignin is provided in the form of nanoparticles and/or microparticles. In some embodiments, providing the lignin comprises providing technical lignin, including but not limited to lignosulfonates, unhydrolyzed Kraft black liquor lignin, hydrolysis lignin, etc. In other embodiments, providing the lignin comprises providing unhydrolyzed lignin and hydrolyzing the lignin to provide hydrolyzed lignin.

In some embodiments, providing the lignin further comprises adjusting the solids content of the lignin. In some embodiments, the solids content may be adjusted by evaporation and/or by adding lignin powder to the aqueous suspension (e.g. to increase the solids content). In other embodiments, the solids content may be adjusted by any suitable means.

In some embodiments, the solids content of the lignin may be adjusted to between about 33% to about 55%, for example, if the composition is to be used in an application in which it's preferable that the composition be flowable. In some embodiments, the solids content may be adjusted to about 46%. In other embodiments, the solids content may be adjusted to about 85% to about 90%, for example, if the composition is to be used as a slurry.

At block 104, at least one isolated strain of bacteria capable of biosurfactant production is provided. The term "provide" in this context may refer to isolating, culturing, receiving, buying, or otherwise obtaining at least one isolated strain. The at least one isolated strain may be any of the isolated strains described above. In some embodiments, the isolated strain is provided in the form of a liquid suspension. In other embodiments, the isolated strain is provided in a freeze-dried form. In other embodiments, the isolated strain is provided in the form of heat-killed cells or a lysate.

At block 106, the lignin is combined with the isolated strain. In some embodiments, the lignin may be combined with the isolated strain by adding the isolated strain to the lignin. In other embodiments, the lignin may be added to the isolated strain. The lignin and the isolated strain may be mixed together using any suitable means.

In some embodiments, the method 100 further comprises gasifying (aerating) the composition. In some embodiments, the composition is gasified after the lignin is combined with the isolated strain. In other embodiments, the isolated strain is gasified and then combined with the lignin. In some embodiments, the isolated strain is aerated with nanobubbles and/or microbubbles. In some embodiments, the isolated strain is aerated with nanobubbles and/or microbubbles using a venturi tube, nano- or microbubble nozzle, or any other suitable device.

In some embodiments, the method 100 further comprises incubating the composition under conditions that allow for proliferation of the at least one isolated strain. In some embodiments, the composition may be incubated for at least one week. In some embodiments, incubating the composition allows the isolated strain to secrete at least a portion of biosurfactant(s) into the composition prior to use.

Figure 2:
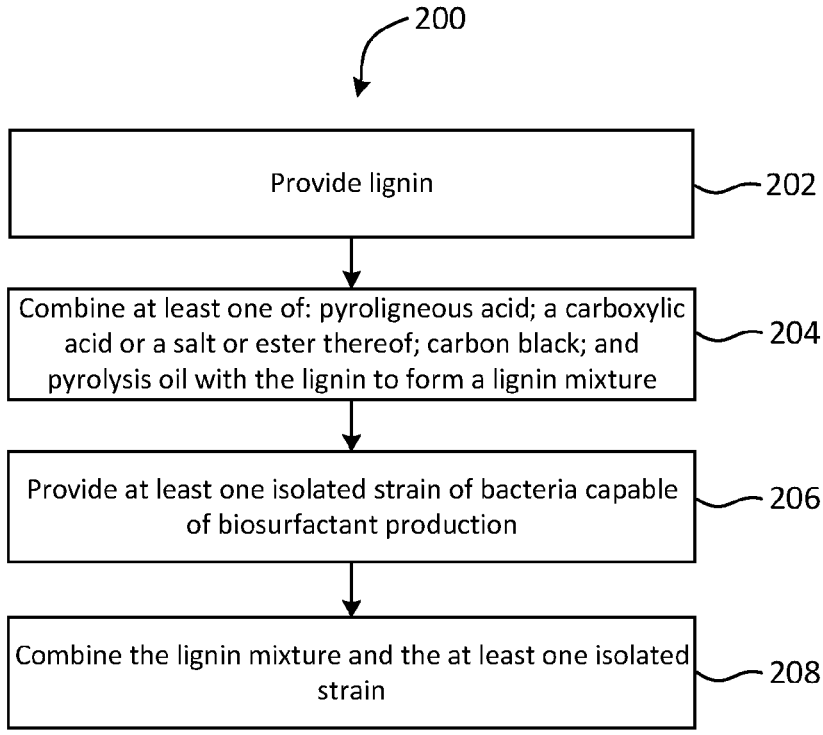
FIG. 2 is a flowchart of another example method for making a composition for separating hydrocarbons from a hydrocarbon-containing material, according to some embodiments.

FIG. 2 shows a flowchart of another example method 200 according to some embodiments, showing additional steps for incorporation of additional components into the composition.

At block 202, lignin is provided. The steps at block 202 may be similar to the steps at block 102 of the method 100 as described above. In this example, the lignin is provided as an aqueous suspension.

At block 204, at least one of a catholyte solution, pyroligneous acid, a carboxylic acid (or a salt or ester thereof), carbon black, and pyrolysis oil is combined with the lignin to form a lignin mixture. In some embodiments, all five of these components are combined with the lignin. In other embodiments, one or more components may be omitted. In some embodiments, each component may be added individually to the lignin in any order. In some embodiments, the lignin mixture may be mixed after addition of each individual component. In other embodiments, the individual components may be combined and the combination of components may be added to the lignin and mixed therein.

At block 206, at least one isolated strain of bacteria capable of biosurfactant production is provided. The steps at block 206 may be similar to the steps at block 104 of the method 100 as described above.

At block 208, the at least one isolated strain is combined with the lignin mixture. The steps at block 208 may be similar to the steps at block 106 of the method 100 as described above.

The method 200 may reduce the risk that the viability of the isolated strain may be detrimentally affected by direct contact of the bacteria with undiluted pyroligneous acid. By adding the pyroligneous acid (and other components) to the lignin prior to combining the lignin with the at least one isolated strain, the pyroligneous acid may be diluted in the lignin (and other components) thereby preventing direct contact of the undiluted pyroligneous acid with the bacteria of the isolated strain.

In some embodiments, the method 200 may comprise any of the other steps described above for the method 100.

EXAMPLES

The invention will now be described in even more detail, by way of example only, with reference to the following non-limiting examples.

Example 1—Phase Separation of Hydrocarbon/Water/Sand Emulsions at Ambient Temperature The performance of an exemplary composition in separating hydrocarbon/water/sand emulsions at ambient temperature was investigated. The emulsions were made using light and heavy oil samples. The ratio of water/oil in the emulsion was the other variable that was tested.

The exemplary composition was labeled as "ActiVata X" and comprised 40-55% liquid sodium lignosulfonate (molecular formula: $C_{20}H_{24}Na_2O_{10}S_2$, CAS number: 8061-51-6) and a combination of isolated strains of biosurfactant-producing bacteria.

All the experiments in this Example were conducted at laboratories of Hydrates, Flow Assurance & Phase Equilibria group, Heriot-Watt University.

Experimental Materials and Methods

To conduct the experiments, the following substances were used to prepare the emulsions: sand; a light oil sample, a heavy oil sample, distilled water, and ActiVata X.

The performance of ActiVata X in separation of hydrocarbon from emulsions of oil/water/sand was investigated using a static emulsion stability measurement method. The investigations were conducted for emulsions prepared using different oil samples at two water/oil ratios. In order to have a more accurate conclusion, in each case, samples containing ActiVata X (referred to as "experimental sample") were compared against similar samples without this additive (referred to as "reference sample"). Therefore, employing the procedure described below, experimental samples and reference samples were prepared.

Reference sample preparation: To prepare the reference sample, 40 wt. % of the oil, 40 wt. % of water, and 20 wt. % of sand were mixed in a beaker using a dispersion unit (IKA T18 basic-ULTRA TURRAX). The mixing process was continued at 10000 rpm for light oil samples/6000 rpm for heavy oil samples for 5 minutes.

Experimental sample preparation: The experimental samples were made by mixing 39 wt. % of the oil, 39 wt. % of water, 2 wt. % ActiVata X and 20 wt. % of sand. Similar to the reference sample preparation, the mixture was then mixed at 10000 rpm for light oil samples/6000 rpm for heavy oil samples for 5 minutes.

The reference and experimental samples were used to prepare emulsions with varying water content as described below.

Emulsion of light oil (without water): The reference and experimental samples were prepared with light oil as described above. No extra water was added to the samples before final mixing.

Emulsion of light oil+100 wt. % water: The reference and experimental emulsions were prepared with light oil. 100 wt. % water was added prior to the final mixing. Final reference and experimental emulsions were observed to check for any phase changes.

Emulsion of light oil+51.8% water: The reference and experimental samples were prepared with light oil. 51.8% wt. % water was added prior to the final mixing.

Emulsion of heavy oil+100 wt. % water: The reference and experimental emulsions were prepared with heavy oil. 100 wt. % water was added to the samples and then the samples were mixed for 5 minutes at 6000 rpm. Final reference and experimental emulsions were observed over time to check for any phase changes.

Sand sample: To check the amount of sand suspended in the separated oil from the light oil emulsion, a sample was taken from the oil phase in the experimental light oil emulsion with 51.8 wt. % additional water. The oil sample was then washed a few times in a paper filter using pure decane to wash out oil from sand grains. A similar procedure was performed at the same time for a sample taken from the reference light oil emulsion with 51.8 wt. % additional water.

Experimental Results and Discussion

The results of the experiments can be categorized based on the type of oil used for the preparation of the emulsion and the oil/water ratio in the final emulsion.

Light oil without extra water: Although for the reference sample, phase separation was very slow, for the experimental sample oil phase separation happened much faster. Percentage of water separated at different times for the experimental sample are tabulated in Table 1. The total volume of water separated from the reference sample after 72 hours was less than 3%.

TABLE 1

| Time (minutes) | 100 | 370 | 440 | 4140 | 4410 |
|---|---|---|---|---|---|
| Separated Water (vol. %) | 5% | 8% | 9% | 28% | 30% |

Light oil with 100% water: For the reference sample, phase separation started very quickly. Over time, water and sands were separated from the emulsion and suspended sand grains were precipitated at the bottom of the graduated cylinder. This allowed the separated water to be more clear and transparent. In comparison to the reference sample, the experimental sample, which contains 2 wt. % of ActiVata X, seemed to be a stable emulsion and even after a few days, no phase separation was observed.

Light oil with 51.8 wt. % water: For both the experimental and reference sample, phase separation was observed. In respect of the experimental sample, after 13 days a layer of clean sand grains precipitated at the bottom of the beaker. Above the precipitated sand was a layer of separated water, above which an emulsion layer was noted. Over time, the thickness of the emulsion layer reduced due to further separation of water, oil, and sands. Finally, a thick top layer of oil was observed. In addition, based on normal visual inspections, the precipitated sands in the beaker containing ActiVata X look to be cleaner than the precipitated sand grains in the reference sample.

Heavy oil with 100% water: A few minutes after preparation of the samples, phase separation happened in the experimental sample containing ActiVata X.

Sand content of the separated oil: Comparison of the weight percentage of the sand in the samples taken from the reference sample and experimental sample of light oil emulsion in the presence of 51.8 wt. % of water, shows a lower sand concentration in the presence of ActiVata X in the emulsion. For the reference sample, the sand wt. % was found to be 6.6%. However, the measured sand content in the sample containing ActiVata X was 5.4%.

Discussion: As described above, for the emulsions prepared using the light oil sample with 100 wt. % additional water, the presence of ActiVata X was not effective in improving phase separation. The phase separation in the reference emulsion happened fast; however, in the experimental sample a stable emulsion without any separated phases was observed.

For the light oil emulsion with 51.8 wt. % additional water, phase separation was observed in both the reference and the experimental samples. Therefore, ActiVata X may not be an effective demulsifier for light oil. However, results of the sand content measurements in the oil phase showed that in samples containing ActiVata X, less sand was present in the oil phase.

In contrast to the light oil samples, the presence of the ActiVata X in the emulsion of heavy oil was effective for phase separation in the emulsion. Also, for both the heavy and light samples in the presence of ActiVata X, no detectable changes were observed in the oil.

Various modifications besides those already described are possible without departing from the concepts disclosed herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although particular embodiments have been shown and described, it will be appreciated by those skilled in the art that various changes and modifications might be made without departing from the scope of the disclosure. The terms and expressions used in the preceding specification have been used herein as terms of description and not of limitation, and there is no intention in the use of such terms and expressions of excluding equivalents of the features shown and described or portions thereof.

The invention claimed is:

1. A composition comprising i) an aqueous suspension of lignin and ii) at least one isolated strain of bacteria selected from the group consisting of *Bacillus amyloliquefaciens, Bacillus licheniformis, Bacillus pumilus, Bacillus subtilis,* and combinations thereof, the aqueous suspension of lignin having a solid content of about 10% or above and comprising lignin nanoparticles and lignin microparticles, wherein at least 20% of the lignin nanoparticles have a particle size of about 100 nm or less.

2. The composition of claim 1, wherein the lignin is technical lignin.

3. The composition of claim 2, wherein the technical lignin comprises at least one of Kraft lignin, lignosulfonates, soda lignin, organosolv lignins, steam-explosion lignin, enzymatic hydrolysis lignin, or unhydrolyzed Kraft black liquor lignin.

4. The composition of claim 1, wherein the at least one isolated strain of bacteria is in the form of a liquid suspension or freeze-dried spores.

5. The composition of claim 1, further comprising a stabilized or enhanced catholyte solution, the catholyte solution having been stabilized or enhanced in a pre-treatment system arranged to introduce nitrogen gas, in the form of nanobubbles and/or microbubbles, into the catholyte solution.

6. The composition of claim 1, further comprising at least one of a carboxylic acid or a salt or ester thereof.

7. The composition of claim 6, wherein the carboxylic acid ester comprises a methyl ester or a butyl ester.

8. The composition of claim 6, wherein the carboxylic acid or salt or ester thereof comprises a di-carboxylic acid or a salt or ester thereof.

9. The composition of claim 1, further comprising carbon black.

10. The composition of claim 1, wherein the composition is gasified.

11. The composition of claim 10, wherein the composition is gasified with at least one of nanobubbles and microbubbles.

* * * * *